United States Patent
Jiang et al.

(10) Patent No.: US 8,781,589 B1
(45) Date of Patent: Jul. 15, 2014

(54) METHOD OF BONDING ZIRCONIA TO PLATINUM

(71) Applicant: Alfred E. Mann Foundation for Scientific Research, Santa Clarita, CA (US)

(72) Inventors: Guangqiang Jiang, Valencia, CA (US); Attila Antalfy, Bristol (GB)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 0 days.

(21) Appl. No.: 13/872,504

(22) Filed: Apr. 29, 2013

Related U.S. Application Data

(62) Division of application No. 11/691,293, filed on Mar. 26, 2007, now Pat. No. 8,447,402.

(60) Provisional application No. 60/787,875, filed on Mar. 31, 2006.

(51) Int. Cl.
*B23K 31/00* (2006.01)
*A61N 1/00* (2006.01)
*A61N 1/375* (2006.01)
*B23K 1/00* (2006.01)
*B32B 15/04* (2006.01)

(52) U.S. Cl.
USPC ............ 607/36; 428/621; 228/246; 607/115; 600/373

(58) Field of Classification Search
None
See application file for complete search history.

(56) References Cited

U.S. PATENT DOCUMENTS

| | | | | |
|---|---|---|---|---|
| 4,991,582 A | * | 2/1991 | Byers et al. | 607/2 |
| 5,193,540 A | * | 3/1993 | Schulman et al. | 607/61 |
| 6,989,200 B2 | * | 1/2006 | Byers et al. | 428/621 |
| 7,114,502 B2 | * | 10/2006 | Schulman et al. | 128/899 |
| 7,132,173 B2 | * | 11/2006 | Daulton | 428/621 |

FOREIGN PATENT DOCUMENTS

WO    WO 2000/056677    *    9/2000    ........... B23K 31/00

OTHER PUBLICATIONS

J. H. Schulman, J. P. Mobley, J. Wolfe, E. Regev, C. Y. Perron, R. Ananth, E. Matei, A. Glukhovsky, R. Davis, "Battery Powered BION FES Network", Sep. 1-5, 2004, Proceedings of the 26th Annual International Conference of the IEEE EMBS, 0-7803-8439-3/04, pp. 4283-4286.*

J. H. Schulman, J. P. Mobley, J. Wolfe, E. Regev, C. Y. Perron, R. Ananth, E. Matei, A. Glukhovsky, R. Davis, "Battery Powered BION FES Network", Sep. 1-5, 2004, Proceedings of the 26th Annual International Conference of the IEEE EMBS, 0-7803-8439-3/04, pp. 4283-4286, published 2004. [document submitted in previous action on Nov. 6, 2013].*

* cited by examiner

*Primary Examiner* — Carl H Layno
*Assistant Examiner* — Erin Piateski
(74) *Attorney, Agent, or Firm* — Gary D. Schnittgrund

(57) ABSTRACT

The invention is a method of hermetically bonding a ceramic part to a metal part by welding and brazing a component assembly comprised of metal parts, a ceramic part, and a metal ferrule having alignment lips. The ceramic part is preferably a hollow tube of partially-stabilized zirconia that is brazed to an alignment ferrule that is preferably titanium or a titanium alloy, such as Ti-6Al-4V. On one end the component assembly is brazed to an end cap for closure. On the other end the alignment ferrule is preferably brazed to a ring that is preferably comprised of a noble metal, such as platinum, iridium, or alloys of platinum and iridium. The ring is laser welded to an eyelet that is preferably comprised of a noble metal.

4 Claims, 2 Drawing Sheets

METHOD OF BONDING ZIRCONIA TO PLATINUM

CROSS-REFERENCE TO RELATED APPLICATION

This application is a divisional application of application Ser. No. 11/691,293 that was filed on Mar. 26, 2007, now U.S. Pat. No. 8,447,402, which claims the benefit of U.S. Provisional Application Ser. No. 60/787,875, filed on Mar. 31, 2006.

BACKGROUND OF THE INVENTION

1. Field of the Invention

This invention relates to a bonded assembly of zirconia ceramic to platinum or other noble metal that employs an alignment ferrule comprised of titanium or an alloy of titanium. The assembly is suitable for implantation in living tissue.

2. Description of Related Art Including Information Disclosed Under 37 CFR 1.97 and 1.98

This invention is concerned with achieving a hermetic bond for an implantable medical device, where the bond is between a ceramic, preferably partially stabilized zirconia, and a noble metal, preferably platinum. A titanium or titanium alloy alignment ferrule provides a transition to allow a noble metal ring to be brazed to the alignment ferrule which is in turn welded to a noble metal eyelet or end cap. It is known that noble metal can be bonded by brazing to ceramic, U.S. Pat. No. 6,989,200. However, this has only been successful with butt joints and has not been previously demonstrated with step and lap joints, as required for certain applications such as where parts require self-centering.

It is desired that the end cap and eyelet, which are electrodes for contact with living tissue when implanted, can sustain high current density and have low impedance, as available only with noble metals, such as platinum, iridium, or their alloys.

DETAILED DESCRIPTION OF THE INVENTION

Figure 1:
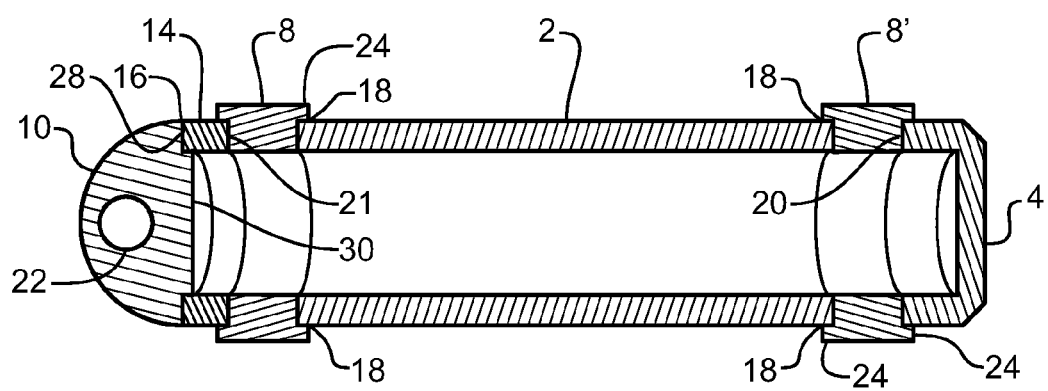
FIG. 1 illustrates a cross-sectional view of a hollow microstimulator case assembly illustrating the improved attachment.

FIG. 1 provides a cross-sectional view of a preferred embodiment of the component assembly 12. It consists of a ceramic article, preferably a hollow ceramic tube 2 that is bonded to an alignment ferrule 8, 8' which may be placed on each end, a first and a second end, respectively, of the hollow ceramic tube 2 by brazing to form braze joint 18. The ceramic is preferably comprised of a partially stabilized tetragonal zirconia polycrystal, which contains about 3 volume percent yttria. U.S. Pat. Nos. 3,594,895; 3,994,430; 6,221,513; 6,521,350; 6,986,453; and 6,989,200 disclose applicable brazing methods and are incorporated herein by reference in their entirety. The alignment ferrule(s) 8, 8' are preferably comprised of titanium or a titanium alloy, such as Ti-6Al-4V. The ceramic tube is preferably a hollow cylinder but may be solid in an alternative embodiment.

The alignment ferrule 8 is joined to a ring 14, which is optionally preferably hollow, and may be solid. Ring 14 is preferably comprised of a noble metal which is biocompatible, such as platinum, iridium, and alloys of platinum and iridium, such as platinum-10 percent by weight iridium.

An eyelet 10 is metallurgically joined to the ring 14, preferably by welding and more preferably by laser welding. As presented, the eyelet 10 optionally has an eyelet hole 22 which facilitates attachment of a removal device, such as a string. In an embodiment wherein the alignment ferrule 8 and the ring 14 are hollow, then the eyelet 10 serves to close-out and hermetically seal the hollow ceramic tube 2, thereby protecting any electronics package that is in tube 2.

As presented in FIG. 1, the eyelet 10 would be associated with and would therefore act as the stimulation anode in an implantable biomedical microstimulator, which results when electronic circuitry is placed inside the ceramic tube 2. Known miniature monitoring and/or stimulating devices for implantation in a living body are disclosed in U.S. Pat. Nos. 6,164,284; 6,185,452; 6,208,894; 6,315,721; 6,564,807; and their progeny, each of which is incorporated herein by reference in its entirety. Typical dimensions for this device are about 5 to 60 mm in length and about 1 to 6 mm in diameter. A coating of iridium may alternately be applied to the titanium alignment ferrule 8 to facilitate tissue contact at the anode end of the component assembly 12.

The second end of the ceramic tube 2 is bonded, preferably by brazing, to an alignment ferrule 8'. The alignment ferrule 8' is bonded, preferably by brazing to an end cap 4, which in a preferred embodiment is comprised of a noble metal, such as platinum, iridium, and alloys of platinum and iridium, such as platinum-10 percent by weight iridium. The end cap 4 is preferably the cathode end of the stimulator, as discussed above.

The joining of the alignment ferrule(s) 8, 8' by brazing to the zirconia tube 2 is accomplished to yield a braze joint 18. In a preferred embodiment nickel foil is the interlayer braze material. In an alternate embodiment, the interlayer braze foil is comprised of a laminate of nickel and titanium. One preferred laminate is obtained from Morgan Advanced Ceramics and is called TiNi-50.

At the second end, the alignment ferrule 8' is preferably bonded by brazing with nickel foil as the interlayer thereby creating braze joint 20 between alignment ferrule 8' and end cap 4.

At the first end the ring 14 is braze bonded using a nickel foil to form braze joint 21 between alignment ferrule 8 and platinum ring 14. The platinum ring 14 is welded by laser to form laser weldment 16 to the platinum eyelet 10.

Figure 2:
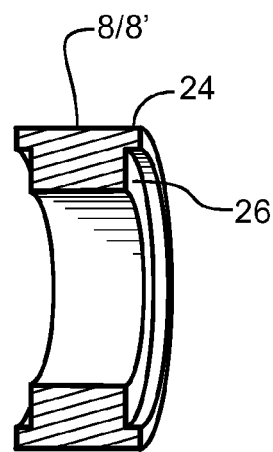
FIG. 2 illustrates a perspective view of an alignment ferrule.

The alignment ferrule(s) 8, 8' are presented in FIG. 2. As discussed, the ferrule is preferably comprised of titanium or in an alternative embodiment Ti-6AL-4V. Either material can be brazed to zirconia ceramic and brazed to platinum or another of the noble metals. A further novel feature of the alignment ferrule 8, 8' is that it is self-aligning in that the lip 24 which in combination with the ferrule face 26 provides a positive alignment of the ferrule 8, 8' on both the ceramic tube and the mating metal part. For example alignment ferrule 8' mates in excellent alignment, without use of a fixture, to the tube 2 and to the end cap 4. Similarly, the alignment ferrule 8 mates to the tube 2 as well as to the ring 14 without use of a fixture.

Figure 3:
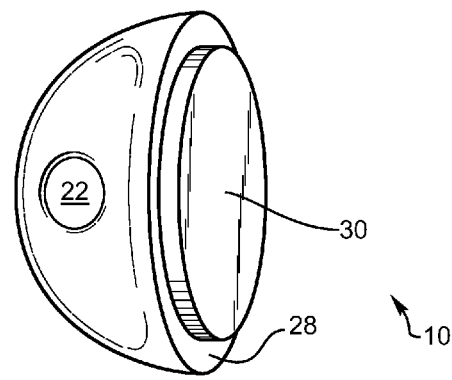
FIG. 3 illustrates a perspective view of an eyelet.

The eyelet 10 also is self-aligning with the ring 14, FIG. 3. The eyelet 10 has a raised alignment tab 30 which is sized to fit inside the ring 14, thereby assuring excellent alignment without the use of a fixture for the welding process. The alignment face 28 of the eyelet 10 mates with the ring 14 to allow formation of laser weldment 16.

It is obvious to those skilled in the art of metallurgical bonding and brazing that the order of assembly is not invariant and may be dictated by good engineering practice.

Figure 4:
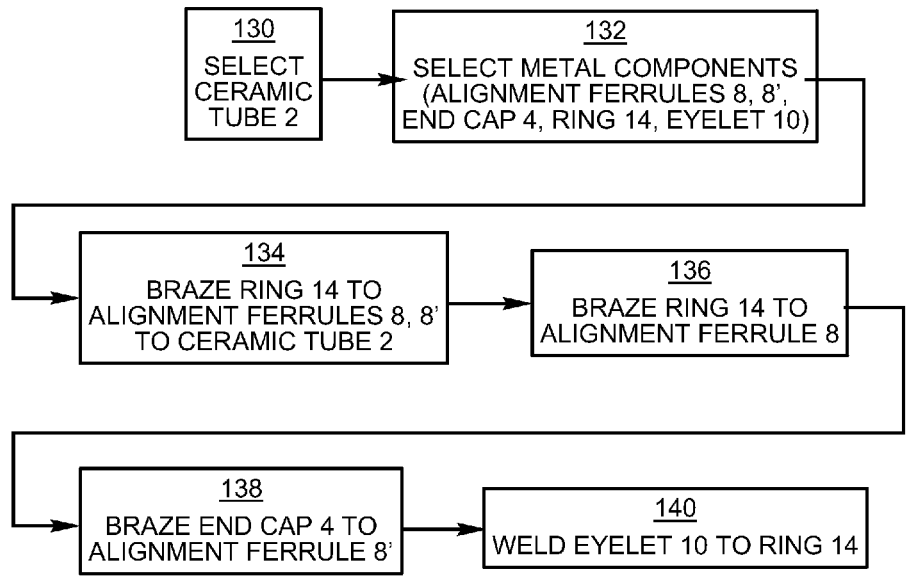
FIG. 4 presents a flow diagram for a method of component assembly.

However, it has been learned through experimentation that the steps represented schematically in FIG. 4 as steps 134, 136, and 138 must be performed in a single braze operation simultaneously. At the second end, the end cap 4 may be bonded to the alignment ferrule 8' at the same time that the alignment ferrule 8' is bonded to the ceramic tube 2. Similarly, at the first end, the ring 14 may be bonded to the alignment ferrule 8 in a single operation, when the alignment ferrule 8 is bonded to the ceramic tube 2. The ring 14 is also bonded to the alignment ferrule 8 and the end cap 4 is bonded to the alignment ferrule 8' before an electronics package is placed inside the assembly 12. Then the preferred last step is to laser weld the eyelet 10 to the ring 14. In this manner high temperature brazing operations are conducted without the electronics being present and thereby avoiding submission of the electronics to a high and damaging temperature. The laser welding operation preferably bonds a platinum eyelet 10 to a platinum ring 14, thus avoiding temperature induced damage to any packaged electronics.

A method of forming the component assembly 12 is presented in FIG. 4. In step 130 a ceramic tube 2 is selected and is preferably partially stabilized tetragonal zirconia polycrystal. This material is strong and bonds by brazing to titanium and titanium alloys.

In step 132 metal components are selected, specifically the alignment ferrules 8, 8', end cap 4, eyelet 4, and ring 14 are selected from biocompatible materials that can be bonded together to from a hermetic component assembly 12. In a preferred embodiment, as discussed previously, the alignment ferrules 8, 8' are comprised of titanium or a titanium alloy. They also have a lip 24 and ferrule face 28 to facilitate self-alignment.

The end cap 4 is comprised of a noble metal, preferably platinum. It is sized to fit snugly to the ferrule face 26 and to contact the lip 24 of the alignment ferrule 8'.

The ring 14 is selected to fit snugly in the alignment ferrule 8 and to contact the ferrule face 26 and to contact the lip 24. It is comprised of a noble metal, preferably platinum.

The eyelet 10 is selected to contact the ring 14. The eyelet 10 is comprised of a noble metal, preferably platinum. It is selected to self-align with the ring 14 by alignment tab 30 fitting snugly inside the hollow ring 14.

In step 134 the alignment ferrules 8, 8' are brazed to the ceramic tube 2 of step 130.

In step 136 the ring 14 is brazed to the alignment ferrule 8. A hermetic bond results with braze joint 21 forming. The platinum ring is readily brazed to the titanium alignment ferrule.

In step 138 the end cap 4 is metallurgically bonded, preferably by brazing, to alignment ferrule 8'. Lastly, eyelet 10 is metallurgically bonded, preferably by welding and most preferably by laser welding, to ring 14. The resulting component assembly 12 is thus hermetically sealed and ready for implantation in living tissue.

Steps 134, 136, and 138 are performed in a single braze operation simultaneously. This step is performed at about $10^{-4}$ Torr or higher vacuum. This simultaneous processing avoids detrimental formation of intermetallics that would occur upon reheating leading to a loss of strength and hermeticity in the joints. After braze bonding the assembly is vacuum cooled to room temperature in the furnace to avoid oxidation of the titanium, which could lead to discoloration and joint brittleness.

Thus, in accordance with this invention, it is now possible to form an implantable hermetically sealed ceramic tube, suitable for containing electronic components, that can serve as a microstimulator or a microsensor by a low-cost, high yield process that utilizes bonding processes for zirconia, titanium and platinum components which utilize self-alignment features. This is a surprising result since performing the braze bonding operation stepwise rather than simultaneously resulted in inadequate bond joints for implantation.

Obviously, many modifications and variations of the present invention are possible in light of the above teachings. It is therefore to be understood that, within the scope of the appended claims, the invention may be practiced otherwise than as specifically described.

GLOSSARY

Terms are generally to be interpreted within the context of the specification and claims. The following terms of art are defined and are to be interpreted by these definitions. Terms that are not defined here shall be interpreted according to definitions from the ASM Metals Reference Book, $3^{rd}$ Edition, 1993, which is included by reference in its entirety.

Biocompatible. The ability of a long-term implantable medical device to perform its intended function, with the desired degree of incorporation in the host, without eliciting any undesirable local or systemic effects in that host. Regulatory agencies require that implanted objects or devices within the human body be biocompatible.

Bond. In welding, brazing, or soldering, the junction of joined parts. Where filler metal is used, it is the junction of the fused metal and the heat-affected base metal.

Braze. Bonding by heating an assembly to suitable temperature and by using a filler metal having a liquidus above 450° C. (840° F.) and below the solidus of the base metal. The filler metal is distributed between the closely fitted faying surfaces of the joint by capillary action.

Butt joint. A joint between two abutting members lying approximately in the same plane.

Filler metal. Metal added in making a brazed, soldered, or welded joint.

Foil. Metal in sheet form less than 0.15 mm (0.006 inches) thick.

Hermetic. Completely sealed by fusion, soldering, brazing, etc., especially against the escape or entry of air or gas.

Implant. To insert or embed an object or a device surgically.

Interlayer. See Foil.

Joined. Fastened together by brazing, welding, or soldering.

Liquidus. In a phase diagram, the locus of points representing the temperatures at which the various compositions in the system begin to freeze on cooling or finish melting on heating.

Microstimulator. An implantable, biocompatible device having dimensions that are less than about 6 mm diameter and 60 mm in length that is capable of sensing or stimulating electrical signals within living tissue.

Noble metal. A metal with marked resistance to chemical reaction, particularly to oxidation and to solution by inorganic acids.

Roll bonding. The same as roll welding and forge welding. A solid-state process where metals are forced together while hot by applying very high pressure that is asserted by rolls to form plate, sheet or foil material and not complex shapes. No filler material is used to achieve roll bonding.

Soldering. A group of processes that join metals by heating them to a suitable temperature below the solidus of the base metals and applying a filler metal having a liquidus not exceeding 450° C. (840° F.). Molten filler metal is distributed between the closely fitted surfaces of the joint by capillary action.

Solid-state welding. A group of processes that join metals at temperatures essentially below the melting points of the base materials, without the addition of a brazing or soldering filler metal. Pressure may or may not be applied to the joint.

Solidus. In a phase diagram, the locus of points representing the temperatures at which various composition stop freezing upon cooling or begin to melt upon heating.

What is claimed is:

1. A method of forming a hermetically sealed partially stabilized tetragonal zirconia polycrystalline ceramic tube and a metal component assembly for use in living tissue, comprising the steps of:
   selecting a partially stabilized tetragonal zirconia polycrystalline ceramic tube comprised of about 3 percent yttria;
   selecting at least one metal alignment ferrule comprised of titanium or titanium alloy that is adapted for self-centering alignment of said ceramic tube in said metal alignment ferrule;
   selecting a ring and an eyelet both comprised of a noble metal for aligning and metallurgically bonding by welding said ring to said eyelet;
   selecting said metal alignment ferrule comprising at least one integral lip that enables the self-centering alignment of said ceramic tube in said metal alignment ferrule and said ring in said metal alignment ferrule;
   selecting a second metal alignment ferrule having at least one second integral lip and selecting an end cap for bonding to said second metal alignment ferrule;
   simultaneously heating said ceramic tube in said metal alignment ferrule that abuts said ring and eyelet assembly and said second metal alignment ferrule abutting said end cap to effect a metallurgical bond and metallurgically bonding said ring to said metal alignment ferrule forming said hermetically sealed component assembly; and wherein
   said step of metallurgically bonding said ceramic tube to said metal alignment ferrule and bonding said ring to said metal alignment ferrule is brazing.

2. A method of forming a hermetically sealed partially stabilized tetragonal zirconia polycrystalline ceramic tube and a metal component assembly for use in living tissue, comprising the steps of:
   selecting a partially stabilized tetragonal zirconia polycrystalline ceramic tube comprised of about 3 percent yttria;
   selecting at least one metal alignment ferrule comprised of titanium or titanium alloy that is adapted for self-centering alignment of said ceramic tube in said metal alignment ferrule;
   selecting a ring and an eyelet both comprised of a noble metal for aligning and metallurgically bonding by welding said ring to said eyelet;
   selecting said metal alignment ferrule comprising at least one integral lip that enables the self-centering alignment of said ceramic tube in said metal alignment ferrule and said ring in said metal alignment ferrule;
   selecting a second metal alignment ferrule having at least one second integral lip and selecting an end cap for bonding to said second metal alignment ferrule;
   simultaneously heating said ceramic tube in said metal alignment ferrule that abuts said ring and eyelet assembly and said second metal alignment ferrule abutting said end cap to effect a metallurgical bond and metallurgically bonding said ring to said metal alignment ferrule forming said hermetically sealed component assembly; and
   the method further comprising the step of selecting said end cap that is comprised of a noble metal and a second metal alignment ferrule with at least one second alignment lip that are braze bonded to said ceramic tube.

3. A method of forming a hermetically sealed component assembly for implantation in living tissue, comprising the steps of:
   selecting an alignment ferrule comprised of titanium or titanium alloy and a ceramic tube;
   selecting a ring comprised of noble metal that further comprises at least one integral lip that enables alignment of said ceramic part and said ring;
   selecting a second alignment ferrule having at least one second integral lip and selecting an end cap for bonding to said alignment ferrule;
   selecting an eyelet having an alignment tab and alignment face to align said ring for bonding;
   selecting an interlayer foil comprised of nickel or nickel-titanium laminate;
   placing said interlayer foil between said ceramic tube, said alignment ferrule, said ring and said abutting eyelet and between said ceramic tube, said second alignment ferrule and said end cap to form said component assembly;
   heating said component assembly in vacuum to braze bond the hermetically sealed component assembly; and
   cooling said component assembly to room temperature.

4. The method according to claim 3, wherein the step of selecting a ring comprised of noble metal is selecting a ring comprised of platinum or iridium or alloys of platinum and iridium.

* * * * *